US012036187B2

(12) United States Patent
Dixon et al.

(10) Patent No.: US 12,036,187 B2
(45) Date of Patent: Jul. 16, 2024

(54) COMPOSITIONS OF DIMETHYL TRISULFIDE (DMTS) AS A CYANIDE ANTIDOTE (71) Applicant: Southwest Research Institute, San Antonio, TX (US)

(72) Inventors: Hong Dixon, Helotes, TX (US); Joseph A. McDonough, Helotes, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 811 days.

(21) Appl. No.: 16/814,988

(22) Filed: Mar. 10, 2020

(65) Prior Publication Data

US 2020/0345658 A1 Nov. 5, 2020

Related U.S. Application Data (60) Provisional application No. 62/841,361, filed on May 1, 2019.

(51) Int. Cl.
*A61K 31/10* (2006.01)
*A61K 9/00* (2006.01)
*A61K 9/107* (2006.01)
*A61M 5/20* (2006.01)

(52) U.S. Cl.
CPC ............ *A61K 31/10* (2013.01); *A61K 9/0019* (2013.01); *A61K 9/1075* (2013.01); *A61M 5/20* (2013.01)

(58) Field of Classification Search
CPC ...... A61K 31/10; A61K 47/10; A61K 9/0019; A61K 9/08; A61K 9/1075; A61M 5/20; A61M 5/30; A61M 5/3157
See application file for complete search history.

(56) References Cited

U.S. PATENT DOCUMENTS

| 9,375,407 | B2 | 6/2016 | Rockwood et al. |
| 9,456,996 | B2 * | 10/2016 | Petrikovics ............ A61K 33/00 |
| 2014/0120159 | A1 | 5/2014 | Petrikovics et al. |
| 2015/0290143 | A1 | 10/2015 | Petrikovics et al. |
| 2015/0290323 | A1 | 10/2015 | Petrikovics et al. |
| 2015/0297535 | A1 | 10/2015 | Petrikovics et al. |

FOREIGN PATENT DOCUMENTS

WO WO-2007053533 A2 * 5/2007 ......... A61K 38/4846

OTHER PUBLICATIONS

Rice, Basic Clin Pharmacol Toxicol. 2019; 125:289-303 (Year: 2019).*
Prieto, Hindawi Publishing Corporation Journal of Applied Chemistry vol. 2013, Article ID 930356, 10 pages. (Year: 2013).*
International Search Report and Written Opinion dated Dec. 4, 2020, issued in PCT International Patent Application No. PCT/US2020/030799, 11 pages.
Kiss, et al., "Method Development for Detecting the Novel Cyanide Antidote Dimethyl Trisulfide from Blood and Brain, and its Interaction with Blood", Journal of Chromatography B, 1044-1045, 2017, pp. 149-157, Elsevier.
Extended European Search Report from related Application No. 20822063.2, dated Dec. 16, 2022.
First Office Action from related Australian Appln. No. 2020292167 dated Nov. 11, 2022.
C.M.Bartling, et al; "Stability Characterization of a Polysorbate 80-Dimethyl Trisulfide Formulation, a Cyanide Antidote Candidate"; Drugs RD (2016 16:109-127).
"Guidance for Industry. Estimating The Maximum Safe Starting Dose in Initial Clinical Trials For Therapeutics in Adult Healthy Volunteers"; U.S.Department of Health and Human Services Food and Drug Administration, Center for Drug Evaluation and Research (CDER)I Jul. 2005, Pharmacology and Toxicology <<J:\!GUIDANC\5541fnlclnl.doc>> Jul. 6, 05 30 pgs; accessed Feb. 11, 2020.
Office Action from related European Application No. 20822063.2, dated Feb. 27, 2024.

* cited by examiner

Primary Examiner — Jean P Cornet
(74) Attorney, Agent, or Firm — Grossman, Tucker, Perreault & Pfleger, PLLC (57) ABSTRACT The present disclosure is directed at compositions of dimethyl trisulfide (DMTS) suitable for use for treatment of cyanide intoxication. The compositions show particularly useful stability such that the DMTS remains stable for therapeutic use at the identified time periods. The compositions are therefore particularly suitable for use in autoinjectors.

13 Claims, 3 Drawing Sheets

COMPOSITIONS OF DIMETHYL TRISULFIDE (DMTS) AS A CYANIDE ANTIDOTE

CROSS-REFERENCE TO RELATED APPLICATIONS

The present application claims the benefit of the filing date of U.S. Provisional Application Ser. No. 62/841,361, filed May 1, 2019, the teachings of which are incorporated by reference.

GOVERNMENT SUPPORT CLAUSE

This invention was made with United States Government support under Contract Award No. W81XWH-17-P-0308 awarded by the U.S. Army Medical Research and Materiel Command. The Government has certain rights in this invention.

FIELD

The present disclosure is directed at compositions of dimethyl trisulfide (DMTS) suitable for use for treatment of cyanide intoxication.

BACKGROUND

Cyanide intoxication in humans has been identified to lead to cellular hypoxia through the binding of the ferric ($Fe^{3+}$) iron in the cytochrome c oxidase system leading to the collapse of the electron transport chain and thereby inhibiting the efficiency of oxygen transport to the tissues. U.S. Pat. No. 9,375,407 entitled "Dimethyl Trisulfide As A Cyanide Antidote" recites that DMTS alone, or in combination with sodium thiosulfate/magnesium thiosulfate (TS) was administered intramuscularly into mice and concluded that DMTS was superior to the then present therapy of TS both in vitro and in vivo.

In U.S. Pat. No. 9,456,996, entitled "Formulations Of Dimethyl Trisulfide For Use As A Cyanide Antidote" there is disclosure of formulations of dimethyl trisulfide made in an aqueous solvent system that includes water and one or more of a co-solvent, a surfactant, a cyclodextrin, and a phospholipid. The concentration of DMTS is recited to be 10 mg/ml to 100 mg/ml. With regards to surfactant concentration, the patent identifies in FIG. 5 that the surfactant concentration is up to 20 wt. % and that it is not recommended to exceed the 20 wt. % Polysorbate 80 concentration. In addition, the patent states that there were no additional advantages with the 20 wt. % Polysorbate 80 versus the 15 wt. % Polysorbate 80 in the in vivo efficacy studies (Table 3) nor in the stability studies (FIGS. 11A, 11B).

Furthermore, in the paper *Stability Characterization of a Polysorbate* 80-*Dimethylsulfide Formulation, A Cyanide Antidote Candidate*, C. M. Bartling, J. C. Andre, C. A. Howland, M. E. Hester, J. T. Cafmeyer, A. Kerr, I. Petrikovics, G. A. Rockwood, Drugs RD (2016) 15:109-127, it is reported that a significant reduction in concentration of DMTS in a 50 mg/mL (approximately equivalent to 5.0 wt. %) DMTS formulation with approximately 15 wt. % polysorbate was observed, namely 36-58% over the course of 29 weeks when stored at room temperature. The reduction could not be explained by formulation and storage temperature, preparative laboratory, or formulation pH. The instability was attributed at least partially to precipitation and evaporation, along with a combination of factors.

Accordingly, a need is present to provide DMTS compositions as a viable drug for cyanide intoxication that have improved stability as well as at higher concentrations that would otherwise be suitable, e.g., for use in relatively small sized off-the shelf autoinjector. However, DMTS is recognized to suffer from relatively low aqueous solubility and instability.

SUMMARY

A composition comprising, consisting essentially of, or consisting of a mixture of: dimethyl trisulfide at a level of 15 wt. % to 50 wt. %, one or more surfactants present at a level of 20 wt. % to 65 wt. %, an organic co-solvent at a level of 10 wt. % to 55 wt. % and water at a level of 10 wt. % to 55 wt. %.

A method of treating cyanide intoxication in a subject comprising, consisting essentially of, or consisting of administering to a subject who would benefit from such treatment a composition comprising dimethyl trisulfide at a level of 15 wt. % to 50 wt. %, one or more surfactants at a level of 20 wt. % to 65 wt. %, an organic co-solvent at a level of 10 wt. % to 55 wt. % and water at a level of 10 wt. % to 55 wt. %.

An autoinjector comprising an injection volume of 0.15 ml to 5.00 ml, the autoinjector configured to deliver a dose of a composition upon activation by an individual, the composition comprising, consisting essentially of or consisting of dimethyl trisulfide at a level of 15 wt. % to 50 wt. %, one or more surfactants at a level of 20 wt. % to 65 wt. %, an organic co-solvent present at a level of 10 wt. % to 55 wt. %, water present at a level of 10 wt. % to 55 wt. %, and wherein the volume of the composition is in the range of 0.15 ml to 5.00 ml.

A composition comprising, consisting essentially of, or consisting of a mixture of dimethyl trisulfide at a level of 15 wt. % to 50 wt. %, one or more surfactants present at a level of 20 wt. % to 75 wt. %, and an organic solvent present at a level of 10 wt. % to 65 wt. %. The composition optionally contains water at a level of up to and including 5000 ppm.

A method of treating cyanide intoxication in a subject comprising administering to a subject who would benefit from such treatment a composition comprising, consisting essentially of, or consisting of dimethyl trisulfide present at a level of 15 wt. % to 50 wt. %, one or more surfactants present at a level of 20 wt. % to 75 wt. %, and an organic solvent present at a level of 10 wt. % to 65 wt. %. The composition optionally contains water at a level of up to and including 5000 ppm.

An autoinjector comprising an injection volume of 0.15 ml to 5.00 ml, said autoinjector configured to deliver a dose of a water free composition upon activation by an individual, the composition comprising, consisting essentially of or consisting of dimethyl trisulfide at a level of 15 wt. % to 50 wt. %, one or more surfactants at a level of 20 wt. % to 70 wt. %, and an organic solvent present at a level of 10 wt. % to 65 wt. %, and wherein the volume of the composition is in the range of 0.15 ml to 5.00 ml. The composition optionally contains water at a level of up to and including 5000 ppm.

A composition comprising, consisting essentially of, or consisting of a mixture of: dimethyl trisulfide at a level of 10 wt. % to 20 wt. %, sodium chloride at 0.1 wt. % to 10 wt. %, one or more surfactants present at a level of 22 wt. % to 45 wt. %, the balance water. The composition optionally contains an organic solvent at a level of up to and including 5000 ppm. In addition, the dimethyl trisulfide composition is such when stored at a temperature of 20° C. to 25° C. in a sealed ampoule, at least 90% or more of the dimethyl trisulfide remains available for therapeutic use.

A method of treating cyanide intoxication in a subject comprising administering to a subject who would benefit from such treatment a composition comprising, consisting essentially of, or consisting of dimethyl trisulfide at 10 wt. % to 20 wt. %, sodium chloride at 0.1 wt. % to 10 wt. %, one or more surfactants present at a level of 22 wt. % to 45 wt. %, the balance water. The composition optionally contains an organic solvent at a level of up to and including 5000 ppm. In addition, the dimethyl trisulfide composition is such when stored at a temperature of 20° C. to 25° C. in a sealed ampoule, at least 90% or more by weight of the dimethyl trisulfide by weight remains available for therapeutic use.

An autoinjector comprising an injection volume of 0.15 ml to 5.00 ml, said autoinjector configured to deliver a dose of an organic solvent free composition upon activation by an individual, the composition comprising, consisting essentially of or consisting of dimethyl trisulfide at a level of 10 wt. % to 20 wt. %, sodium chloride at 0.1 wt. % to 10 wt. %, one or more surfactants present at a level of 22 wt. % to 45 wt. %, the balance water, and wherein the volume of the composition is in the range of 0.15 ml to 5.00 ml. The composition optionally contains organic solvent at a level of up to and including 5000 ppm. The dimethyl trisulfide composition, when stored at a temperature of 20° C. to 25° C. in the autoinjector provides that at least 90% or more by weight of the dimethyl trisulfide remains available for therapeutic use.

DETAILED DESCRIPTION

The present disclosure identifies compositions, methodology and autoinjectors that can provide a therapeutic amount of DMTS to a subject. The compositions rely upon DMTS and fall into the following three general categories: (I) DMTS at a level of 15 wt. % to 50 wt. %, one or more surfactants, an organic co-solvent and water; (II) DMTS at a level of 15 wt. % to 50 wt. %, one or more surfactants, and an organic solvent, which composition is substantially water free; and (III) DMTS at a level of 10 wt. % to 20 wt. %, one or more surfactants at a level of 22 wt. % to 45 wt. %, sodium chloride and the balance water, which composition is substantially free of organic solvent.

Reference to a composition that is substantially free of any organic solvent herein should be understood as a composition that optionally contains up to and including 5000 ppm of organic solvent, which may occur, e.g. due to the presence of inevitable impurities that may be present in reagents or introduced during preparation. Similarly, reference to a composition that is substantially water free herein should similarly be understood as a composition that optionally contains up to and including 5000 ppm water. The aforementioned limit levels of either organic solvent or water may also preferably be at or below 4000 ppm, at or below 3000 ppm, at or below 2000 ppm, at or below 1000 ppm, at or below 500 ppm, at or below 100 ppm, or at or below 50 ppm. The Category (II) and (III) Compositions described herein may also be such that they are, respectively, compositions that contain substantially no water or substantially no organic solvent. Accordingly, the Category (II) Compositions may preferably be entirely water free and the Category (III) Compositions may preferably be entirely free of organic solvent.

Cyanide intoxication herein is to be understood to mean a medical condition that is characterized by cyanide interference through inhibition of the mitochondrial enzyme cytochrome c thereby inhibiting the efficiency of oxygen transport to the tissues. A pharmaceutical composition herein should be understood as a composition that provides a prescribed dosage to an animal or human.

As noted, the present disclosure also stands directed at a method of treating cyanide intoxication in a subject who would benefit from such treatment involving a therapeutically effective amount of DMTS. The DMTS may preferably be administered by intramuscular (IM), subcutaneous, intravenous, or intraosseous injection or through the nasal passage.

The concentration of DMTS in the solvent system in the category (I) and (II) compositions noted above is preferably in the range of 15 wt. % to 50 wt. %, including all values and ranges therein. For example, the level of DMTS may be in the range of 15 wt. % to 50 wt. %, or 25 wt. % to 50 wt. %, or 30 wt. % to 50 wt. %, or 35 wt. % to 50 wt. %, or 40 wt. % to 50 wt. %, or 45 wt. % to 50 wt. %. One particularly preferred range is 15 wt. % to 35 wt. %.

The concentration of surfactant in the category (I) compositions may range from 20 wt. % to 65 wt. %, including all values and increments therein. For example, more preferably the concentration of surfactant may be in the range of 25 wt. % to 65 wt. %, or 30 wt. % to 65 wt. %, or 35 wt. % to 65 wt. %, or 40 wt. % to 65 wt. %, or 45 wt. % to 65 wt. %, or 50 wt. % to 65 wt. %, or 55 wt. % to 65 wt. %, or 60 wt. % to 65 wt. %. One particularly preferred range is from 20 wt. % to 50 wt. %. Suitable surfactants herein include non-ionic and ionic, with non-ionic preferred. Preferred non-ionic surfactants include hydrogenated castor oil, e.g. KOLLIPHORE® ELP or KOLLIPHORE® HS15 available from BASF Global. Other non-ionic surfactants include polysorbates, such as polysorbate 80, and poloxamer, such as KOLLIPHOR® P188.

The concentration of surfactant in the category (II) compositions may range from 20 wt. % to 75 wt. %, including all values and increments therein. For example, more preferably the concentration of surfactant may be in the range of 25 wt. % to 75 wt. %, or 30 wt. % to 75 wt. %, or 35 wt. % to 75 wt. %, or 40 wt. % to 75 wt. %, or 45 wt. % to 75 wt. %, or 50 wt. % to 75 wt. %, or 55 wt. % to 75 wt. %, or 60 wt. % to 75 wt. %, or 65 wt. % to 75 wt. %. One particularly preferred range is from 20 wt. % to 50 wt. %. Suitable surfactants herein include non-ionic and ionic, with non-ionic preferred. Preferred non-ionic surfactants include hydrogenated castor oil, e.g. KOLLIPHORE® ELP or KOLLIPHORE® HS15 available from BASF Global. Other non-ionic surfactants include polysorbates, such as polysorbate 80, and poloxamer, such as Kolliphor P188.

The organic co-solvent or solvent, when present, preferably includes an organic alcohol, such as ethanol or propylene glycol as well as other water-miscible solvents such as glycofurol, dimethyl isosorbide, diglyme or N-methyl-2- pyrrolidone. The co-solvent may also include polyether compounds with terminal hydroxy groups, such as polyethylene glycol (PEG) preferably at molecular weights in the range of 100 to 20,000, more preferably 100 to 4000. One particularly preferred co-solvent includes PEG 200 which has a molecular weight in the range of 190-210. In the category (1) compositions the organic co-solvent is present at a level of 10 wt. % to 55 wt. %, or 15 wt. % to 55 wt. %, or 20 wt. % to 55 wt. %, or 20 wt. % to 55 wt. %, or 25 wt. % to 55 wt. %, or 30 wt. % to 55 wt. %, or 35 wt. % to 55 wt. %, or 40 wt. % to 55 wt. %, or 45 wt. % to 55 wt. %, or 50 wt. % to 55 wt. %. In the category (2) compositions, the organic solvent is present at 10 wt. % to 65 wt. %, or 15 wt. % to 65 wt. %, or 20 wt. % to 65 wt. %, or 25 wt. % to 65 wt. %, or 30 wt. % to 65 wt. %, or 35 wt. % to 65 wt. %, or 40 wt. % to 65 wt. %, or 45 wt. % to 65 wt. %, or 50 wt. % to 65 wt. %, or 55 wt. % to 65 wt. % or 60 wt. % to 65 wt. %.

The category (I) compositions include water. Water can be present in such compositions at 10 wt. % to 55 wt. %, 15 wt. % to 55 wt. %, 20 wt. % to 55 wt. %, 25 wt. % to 55 wt. %, 30 wt. % to 55 wt. %, 35 wt. % to 55 wt. %, 40 wt. % to 55 wt. %, 45 wt. % to 55 wt. %, 50 wt. % to 55 wt. %.

The category (III) compositions herein are preferably substantially or entirely free of any organic solvent. Such compositions may include DMTS at a level of 10 wt. % to 20 wt. %, or 11 wt. % to 20 wt. %, or 12 wt. % to 20 wt. %, or 13 wt. % to 20 wt. %, or 14 wt. % to 20 wt. %, or 15 wt. % to 20 wt. %, or 16 wt. % to 20 wt. %, or 17 wt. % to 20 wt. %, or 18 wt. % to 20 wt. %, or 19 wt. % to 20 wt. %. The category (3) compositions herein may also preferably include DMTS at a level of 10 wt % to 15 wt. %, 10 wt. % to 14 wt. %, 10 wt. % to 13 wt. %, 10 wt. % to 12 wt. % or 10 wt. % to 11 wt. %. The category (3) compositions also include sodium chloride at a level of 0.1 wt. % to 10 wt. %, more preferably at 0.1 wt. % to 1.0 wt. %, and one or more surfactants, which surfactants are as noted herein. The level of the one or more surfactants are 22 wt. % to 45 wt. %, or 25 wt. % to 45 wt. %, or 30 wt. % to 45 wt. %, or 35 wt. % to 45 wt. % or 40 wt. % to 45 wt. %. The balance of such compositions contain water, and accordingly, the level of water may be 25 wt. % to 67.9 wt. %. The level of water may therefore be at a level of less than 65 wt. %, or less than 60 wt. %, or less than 55 wt. %, or less than 50 wt. %, or less than 45 wt. %, or less than 40 wt. %, or less than 35 wt. % or less than 30 wt. %, or at 25 wt. %. A range of water may therefore include 25 wt. % up to 67.9 wt. %.

Figure 1:
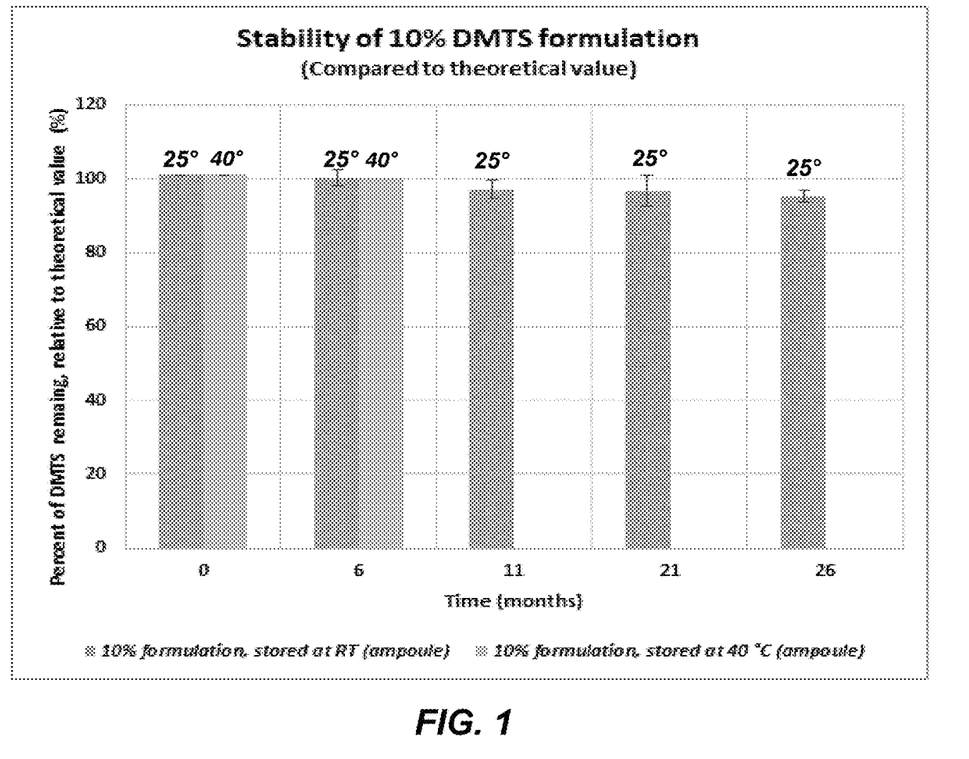
FIG. 1 shows the percent DMTS remaining vs. the indicated time and at the indicated temperatures in a composition initially containing 10 wt. % DMTS, 22 wt. % surfactant, 0.5 wt. % to 0.7 wt. % NaCl, the balance water.

FIG. 1, shows the percent of DMTS remaining in a category (III) composition initially containing 10 wt. % DMTS, 22 wt. % surfactant, 0.5 wt. % to 0.7 wt. % NaCl, the balance water (~67 wt. %) in a sealed ampoule at 25° C. and at 40° C. As can be seen, at 6 months the percent DMTS remaining for therapeutic use was at or greater than or equal to 97-98%. At 25° C. after 11 months, 21 months or 26 months, the percent DMTS remaining for therapeutic use was greater than or equal to 95%.

Accordingly, a composition herein containing DMTS at a level of 10 wt. % to 20 wt %, sodium chloride at 0.1 wt. % to 10 wt. %, one or more surfactants at a level of 22 wt. % to 45 wt. %, with the balance water, and optionally including organic solvent at a level of up to and including 5000 ppm, is such that when stored at 20° C. to 25° C., in a sealed ampoule, at least 90% or more by weight of the DMTS remains available for therapeutic use for a period up to and including 26 months. More preferably, 95% or more by weight of the DMTS is available for therapeutic use for a period of up to and including 26 months when stored at 20° C. to 25° C. in a sealed ampoule. It is therefore contemplated that the above identified composition indicates the same stability and ensuing availability of DMTS for therapeutic use when stored in an autoinjector.

As can also be seen in FIG. 1, at a temperature of 40° C., the subject DMTS composition when stored in a sealed ampoule, shows that 95% or more by weight of the DMTS is available for therapeutic use, for a period of up to and including six months. Once again, it is contemplated that such stability and ensuing availability of DMTS for therapeutic use would be the same when the DMTS is stored in an autoinjector.

It may therefore be appreciated that the above three general compositions are such that they may form or provide a microemulsion. Reference to a microemulsion is reference to the feature that the DMTS droplets in such microemulsion are preferably in the range of 1 nm to 100 nm and appear visually clear or with a slight haze. More preferably, the DMTS droplet in the microemulsions herein may have a size in the range of 1 nm to 75 nm, or even more preferably, in the range of 15 nm to 55 nm. More specifically, when water is present, a microemulsion is formed where the DMTS droplets can have the size range noted herein. Alternatively, when the composition starts water-free, and contains DMTS, surfactant and a co-solvent (e.g. ethanol), it initially is in the form of a solution, that when introduced into water, becomes a microemulsion with the DMTS droplets again having the aforementioned size distribution (1 nm to 100 nm).

The category (I), (II) and (III) compositions are all such that they may be employed in an autoinjector having a volume in the range of 0.15 ml to 5.00 ml. As discussed more fully herein, the compositions are such that they provide a freeze-thaw stability, remain relatively clear without precipitation, and the category (III) compositions show a remarkable stability against degradation to therefore provide an enhanced shelf-life projected out to at least 26 months at ambient temperature and which is projected to be longer at lower temperature (e.g. 2-8° C.) storage.

Example 1

DMTS Composition at 27% DMTS

Category (I) Composition—DMTS In Water/Organic Co-Solvent/Surfactant

A first composition was prepared herein containing 1.49 g DMTS (27 wt. %), 1.97 g KOLLIPHORE® ELP (35.9 wt. %), 1.48 g ethanol (27 wt. %) and 0.54 g deionized water (10 wt. %). The composition was clear and could be sterilized by filtration by passage by passage through a 0.2 μm filter. The composition remained clear for over one month when stored at ambient temperature, and indicated freeze-thaw stability (i.e. it did not freeze at −20° C. and remained clear).

The composition also remained as a microemulsion when added to deionized water or phosphate buffer solution.

Example 2

DMTS Composition t 35% DMTS

Category (II) Composition—DMTS/Organic Solvent/Surfactant

A second composition was prepared herein containing 0.35 g DMTS (35 wt. %), 0.48 g KOLLIPHORE® ELP (47 wt. %) and 0.18 g ethanol (18 wt. %). This composition remained clear for over one month while stored at ambient temperature. The composition and indicated freeze-thaw stability ((i.e. it did not freeze at −20° C. and remained clear). The composition also formed a microemulsion when added to deionized water or phosphate buffer solution. As noted, the Category 2 Compositions are such that they may optionally contain 0-5000 ppm water.

Example 3

DMTS Composition at 10% DMTS

Category (III)
Composition—DMTS/Surfactant/Sodium Chloride/Water

A composition was prepared herein containing 33.7 g DMTS (10 wt. %), 75 g KOLLIPHORE ELP (22 wt. %), in 227 g deionized water (67%), and 0.7 g NaCl (1%) was used to make the composition isotonic. The composition contained over 95% by weight of DMTS after 26 months storage at ambient temperature (20° C. to 25° C.). See again, FIG. 1. This composition therefore has a shelf-life of at least twenty-six months at ambient temperature which shelf life is contemplated to be longer at 2-8° C. storage. As noted, the Category (III) Compositions are such that they may optionally contain 0-5000 ppm of an organic solvent.

The compositions or microemulsions herein, containing DMTS as noted herein, were all observed to be capable of sterilization by filtration through, e.g., a 0.2 μm filter. In addition, the compositions are capable of being utilized in a syringe injector and are therefore suitable for intramuscular, intravenous, or intraosseous injection. In addition, the composition herein appears suitable for nasal delivery (e.g. in an aerosol delivery system).

More specifically, the compositions herein were found particularly suitable for use in relatively small size autoinjector, such as an autoinjector which has an available volume in the range of 0.15 ml to 5.00 ml. A particularly preferred autoinjector herein may therefore have a volume of 2.0 ml to 2.50 ml. It should be noted that reference to an autoinjector herein may be understood as an injector device that, upon actuation (e.g., pressing of a button), a syringe needle is automatically inserted and the subject drug is delivered at a selected dose. Typically, the autoinjector is a spring-loaded device. Preferably, once the injection is complete the autoinjectors may provide an indication to the user to confirm that a particular dose has been delivered. In such context, autoinjectors herein may include gas jet autoinjectors which contain a cylinder of pressurized gas that propels a jet of the liquid dose through the skin without the use of a needle. As noted, the autoinjectors that are preferred for use herein are those that include 0.15 mL to 5.00 ml volume capability. It should also be noted that such autoinjectors are preferably configured herein to include the use of 21-27 gauge needles. It is noted that a 21 gauge needle will have a nominal inner diameter of 0.51 mm. A 22 gauge needle as used herein will have a nominal inner diameter of 0.41 mm. A 23 gauge needle as used herein will have a nominal inner diameter of 0.34 mm and a 24 gauge needle has a nominal inner diameter of 0.31 mm.

Animal Testing

Category 1
Composition—DMTS/Surfactant/Organic Co-solvent/Water

Animal testing was carried-out for the above referenced Category I Composition. As an example, a composition was evaluated that contained 27.1% by weight DMTS, 35.9% by weight Kolliphor ELP, 27.0% by weight ethanol and 10.0% by weight water. As an initial matter, safety was evaluated as shown in Table 1 for the identified mouse studies:

TABLE 1

| Mouse Studies-27% By Weight Aqueous DMTS | | | |
|---|---|---|---|
| Dose (mg/kg) | Number Dosed | Lived | Percent Survival |
| 251 | 2 | 2 | 100% |
| 315 | 4 | 2 | 50% |
| 397 | 4 | 1 | 25% |
| 500 | 1 | 0 | 0% |

Figure 2:
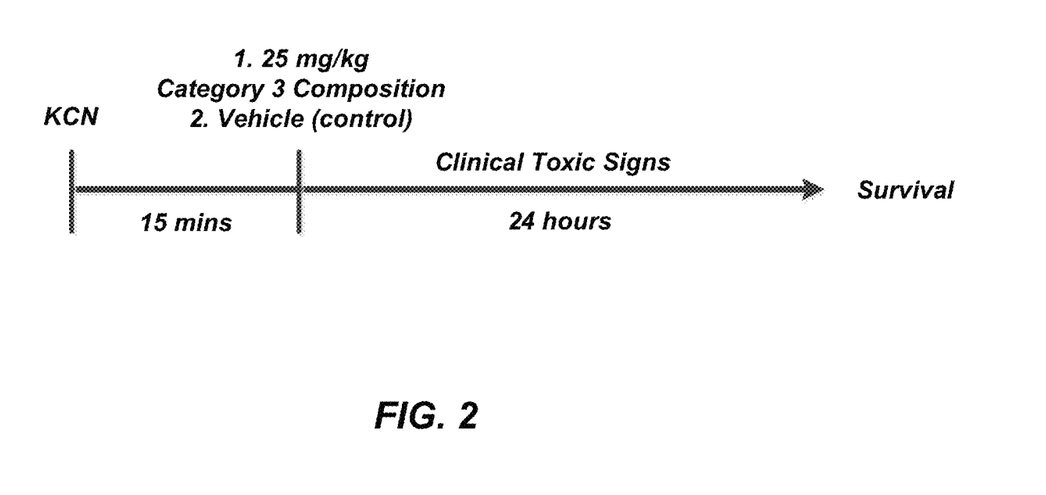
FIG. 2 shows a testing protocol utilized for evaluation of the efficacy of the compositions disclosed herein.

As can be seen from the above, the Category 1 composition herein indicates a safety level corresponding to a $LD_{50}$ value of 328 mg/kg. Animal testing (mouse studies) was then carried-out for the above Category 1 Composition. Specifically, the testing protocol as illustrated in FIG. 2 for the mouse studies versus a vehicle control. The subject 27% aqueous DMTS composition was administered intramuscularly (IM) at a level of 25 mg/kg. The results are shown in Table 2.

TABLE 2

| Mouse Survival Data-Category 1 Composition | | |
|---|---|---|
| KCN Dose (mg/kg) | Number Treated | Lived (Percent) |
| 7.5 | 2 | 2 (100) |
| 9.5 | 3 | 1 (33) |
| 12.0 | 2 | 0 (0) |

In addition, for the Category 1 Composition herein, an antidote potency ratio (APR) was determined, which is the $LD_{50}$ of cyanide treatment with antidote divided by the $LD_{50}$ of cyanide treatment without antidote. The APR was determined to be 1.63, where mpk refers to milligrams per kilogram.

Another Category 1 composition was investigated. Specifically, 15.0% by weight DMTS, 20.0% by weight Kolliphor ELP, 55.0% by weight ethanol and 10.0% water. Safety was evaluated as shown in Table 3 for the identified mouse studies:

TABLE 3

| Mouse Studies-15.0% By Weight Aqueous DMTS | | | |
|---|---|---|---|
| Dose (mg/kg) | Number Dosed | Lived | Percent Survival |
| 251 | 1 | 1 | 100% |
| 315 | 2 | 1 | 50% |
| 397 | 3 | 1 | 33% |
| 500 | 2 | 0 | 0% |

As can be seen from the above, the data suggested an $LD_{50}$ value of >250 mg/kg. Animal testing (mouse studies) was carried out for the above referenced Category 1 Composition. Specifically, the testing protocol was again as illustrated in FIG. 2 for the mouse studies versus a vehicle control. The subject 15% aqueous DMTS composition was administered intramuscularly (IM) at a level of 25 mg/kg. The results are shown in Table 4.

TABLE 4

Mouse Survival Data-Category 1 Composition

| KCN Dose (mg/kg) | Number Treated | Lived (%) |
|---|---|---|
| 7.5 | 2 | 2 (100) |
| 9.5 | 3 | 1 (33) |
| 12.0 | 3 | 1 (33) |
| 15.1 | 2 | 1 (50) |
| 19.0 | 2 | 1 (50) |
| 23.9 | 1 | 0 (0) |

For the above referenced Category 1 Composition, the antidote potency ratio (APR) was determined to be 1.5.

Category 2 Compositions—DMTS/Surfactants/Organic Solvent/Substantially Water Free Animal testing was carried out for the above referenced Category 2 Compositions. As an example, a Category 2 Composition was evaluated that contained 15.0% by weight DMTS, 20.0% by weight Kolliphor ELP and 65.0% by weight ethanol. As an initial matter, safety was evaluated as shown in Table 5 for the identified mouse studies:

TABLE 5

Mouse Studies-15.0% By Weight DMTS (Substantially Water Free)

| Dose (mg/kg) | Number Dosed | Lived | Percent Survival |
|---|---|---|---|
| 251 | 2 | 2 | 100 |
| 315 | 3 | 1 | 33 |
| 397 | 2 | 0 | 0 |
| 500 | 1 | 0 | 0 |

As can be seen from the above, the date suggested an $LD_{50}$ value of >250 mg/kg. Animal testing (mouse studies) was carried out for the above referenced Category 2 Composition. Specifically, the testing protocol was again as illustrated in FIG. 2 for the mouse studies versus a vehicle control. The subject 15% DMTS composition was administered intramuscularly (IM) at a level of 25 mg/kg. The results are shown in Table 6:

TABLE 6

Mouse Survival Data-Category 2 Composition

| KCN Dose (mg/kg) | Number Treated | Lived (Percent) |
|---|---|---|
| 7.5 | 1 | 1 (100) |
| 9.5 | 2 | 1 (50) |
| 12.0 | 4 | 2 (50) |
| 15.1 | 3 | 1 (33) |
| 19.0 | 2 | 1 (50) |
| 23.9 | 1 | 0 (0) |

For the above referenced Category 2 Composition, the antidote potency ratio (APR) was determined to be 1.85.

Category 3 Composition—DMTS/Surfactant/Sodium Chloride/Water

Animal testing was carried-out for the above referenced Category 3 Composition, which as noted, amounts to DMTS at 10 wt. % to 20 wt. %, sodium chloride at 0.1 wt. % to 10 wt. %, surfactants at 22 wt. % to 45 wt. %, the balance water. First, safety of the Category 3 Compositions revealed as follows: Male Mouse: DMTS $LD_{50}$=242 mpk, Female Mouse: DMTS $LD_{50}$=248 mpk. Male Rat; DMTS $LD_{50}$>126 mpk. It is noted that the DMTS $LD_{50}$ in rats could not be determined as higher injection volumes for higher doses exceeded the Institutional Animal Care And Use Committee Regulations.

Efficacy in rodent testing was then conducted. The protocol involved exposure to different does of KCN, a delay of one minute, IM injection of the Category 3 Composition at dosages of 12.5 mg/kg DMTS, 25 mg/kg DMTS and 75 mg/kg DMTS and evaluation of survival after a period of 24 hours. The Category 3 Composition utilized was 33.7 g DMTS (10 wt. %), 75 g KOLLIPHORE ELP (22 wt. %, in 227 g deionized water (67 wt. %) and 0.7 g NaCl (1 wt. %). The results are provided in Tables 7-10 below for male mouse testing at the indicated dosages:

TABLE 7

12.5 mg/kg DMTS

| KCN Dose (mg/kg) | Number Treated | Lived (Percent) |
|---|---|---|
| 9.5 | 1 | 1 (100) |
| 12.0 | 4 | 4 (100) |
| 15.1 | 5 | 2 (40) |
| 19.0 | 9 | 1 (11) |
| 23.9 | 2 | 0 (0) |
| 30.1 | 1 | 0 (0) |

TABLE 8

25 mg/kg DMTS

| KCN Dose (mg/kg) | Number Treated | Lived (Percent) |
|---|---|---|
| 4.8 | 1 | 1 (100) |
| 6.0 | 2 | 2 (100) |
| 7.6 | 3 | 2 (66.6) |
| 9.5 | 3 | 3 (100) |
| 12.0 | 4 | 3 (75) |
| 15.1 | 4 | 3 (75) |
| 23.9 | 3 | 1 (33) |
| 30.1 | 1 | 0 (0) |
| 37.9 | 3 | 0 (0) |
| 47.7 | 2 | 0 (0) |
| 60.1 | 1 | 0 (0) |

TABLE 9

75 mg/kg DMTS

| KCN Dose (mg/kg) | Number Treated | Lived (Percent) |
|---|---|---|
| 7.6 | 1 | 1 (100) |
| 9.5 | 3 | 2 (66.6) |
| 12.0 | 3 | 3 (100) |
| 15.1 | 4 | 3 (75) |
| 19.0 | 6 | 2 (33.3) |
| 23.9 | 4 | 2 (50) |
| 30.1 | 3 | 0 (0) |

TABLE 10

Mouse (Male)

| DMTS (mg/kg) | APR |
|---|---|
| 12.5 | 2.71 |
| 25 | 3.70 |
| 75 | 3.60 |

Results for female mouse testing appear below in Table 11 and 12 for a Category 3 Composition at the dosage of 25 mg/kg DMTS. The Category 1 Composition was 33.7 g DMTS (10 wt. %), 75 g KOLLIPHORE ELP (22 wt. %) in 227 g deionized water (67 wt. %) and 0.7 g NaCl (1 wt. %).

TABLE 11

25 mg/kg DMTS (Female Mouse)

| KCN Dose (mg/kg) | Number Treated | Lived |
| --- | --- | --- |
| 7.9 | 1 | 1 |
| 10.0 | 4 | 3 |
| 12.6 | 4 | 2 |
| 15.9 | 2 | 0 |

TABLE 12

Mouse (Female)

| DMTS (mg/kg) | APR |
| --- | --- |
| 25 | 2.20 |

Animal testing continued utilizing male rats for the Category 3 Compositions. Specifically, 33.7 g DMTS (10 wt. %), 75 g KOLLIPHORE ELP (22 wt. %) in 227 g deionized water (67 wt. %) and 0.7 g NaCl (1 wt. %). Once again, different doses of KCN were administered followed by a one minute delay and then IM administration of the aforementioned DMTS composition at dosages of 12.5 mg/kg and 25 mg/kg. The results appear in Tables 13-15:

TABLE 13

12.5 mg/kg DMTS

| KCN Dose (mg/kg) | Number Treated | Lived |
| --- | --- | --- |
| 16.0 | 3 | 3 |
| 20.1 | 5 | 2 |
| 25.4 | 3 | 1 |
| 21.9 | 1 | 0 |

TABLE 14

25 mg/kg DMTS

| KCN Dose (mg/kg) | Number Treated | Lived |
| --- | --- | --- |
| 16.0 | 1 | 1 |
| 20.1 | 2 | 2 |
| 25.4 | 4 | 3 |
| 31.9 | 3 | 0 |

TABLE 15

Rat (Male)

| DMTS (mg/kg) | APR |
| --- | --- |
| 12.5 | 2.23 |

A second testing protocol, mentioned above, is illustrated in FIG. 2 was conducted on the Category 3 Compositions versus a vehicle control. Once again, 33.7 g DMTS (10 wt. %), 75 g KOLLIPHORE ELP (22 wt. %) in 227 g deionized water (67 wt. %) and 0.7 g NaCl (1 wt. %). The KCN dose was 9.2 mg/kg or 10.2 mg/kg of body weight. After a period of 15 minutes the animals (male rats) were treated with an intramuscular injection (IM) with the above referenced Category 3 Composition. The vehicle control amounted to treatment of KCN with no antidote provided.

Table 16 below provides the results for this study regarding male rat survival data. As can be seen the subject 10 wt. % DMTS composition noted above was preferably administered intramuscularly (IM) at a level of 25 mg/kg.

TABLE 16

Male Rat Survival Data-Category 3 Compositions

| KCN Dose (mg/kg) | Vehicle-Treated Survival | 25 mg/kg (IM) DMTS Treated/Survival (Percent) |
| --- | --- | --- |
| 9.2 | 11/14 | 12/13 (92) |
| 10.2 | 10/15 | 14/15 (93) |

Table 17 below provides the results for this study with regards to time to recovery, where time to recovery is defined as the time at which the disappearance of the most negative clinical toxic signs was observed (not including labored breathing or lethargy). The negative clinical toxic signs included negative righting reflex, negative toe pinch, minor gasping, severe convulsions, minor convulsions, tremors, and shaky ambulation.

TABLE 17

Male Rats Time To Recovery-Category 3 Compositions

| KCN Dose (mg/kg) | Vehicle-Treated Time To Recovery | 25 mg/kg (IM) DMTS Treated Time To Recovery |
| --- | --- | --- |
| 9.2 | 62.6 mins | 25.6 mins |
| 10.2 | 51.8 mins | 26.9 mins |

Next, swine model testing was conducted on the Category 3 Compositions herein. Female swines of 45-50 kg were anesthetized. KCN infusion was applied for a period of about 5 minutes and stopped and an aqueous composition was administered intramuscularly containing 10 wt. % DMTS, sodium chloride at 1.0 wt. %, KOLLIPHOR® ELP at 22.0 wt. %, the balance water. Table 18 below provides the results of the efficacy of such composition across the identified DMTS dose in mg/kg of body weight after KCN infusion and IM injection as noted above:

TABLE 18

Swine Model Testing-Category 3 Compositions

| DMTS mg/kg | Survived | Tested |
| --- | --- | --- |
| 25.0 | 2 | 2 |
| 18.75 | 1 | 1 |
| 12.5 | 1 | 2 |
| 10.0 | 3 | 4 |
| 7.5 | 1 | 1 |

In sum, for the Category 3 Compositions herein, from the swine model testing, suitable dosage levels fall in the range of 7.5 mg/kg to 25.0 mg/kg and all individual values and increments therein. For example, suitable dosage ranges may include 7.5 mg/kg to 10.0 mg/kg or 7.5 mg/kg to 12.5 mg/kg or 7.5 mg/kg to 18.75 mg/kg. Based upon the earlier described mouse testing, effective dosages were observed in the range of 12.5 mg/kg to 75 mg/kg.

Reference is now made to the U.S. Department of Health and Human Services July 2005 publication entitled *Guidance For Industry—Estimating the Maximum Safe Starting Dose in Initial Clinical Trials for Therapeutics in Adult Healthy Volunteers* at page 7. There it is identified that one can convert the animal dose in mg/kg to human doses in mg/kg, for mouse studies, by dividing the animal dose by 12.3 and for swine studies one divides by 1.1. Applying that to the mouse dosage range herein of 12.5 mg/kg to 75 mg/kg of DMTS (Category 3 Composition) converts to a human equivalent dose of 1.0 mg/kg to 6.1 mg/kg. From the above referenced swine studies, the dosage range was 7.5 mg/kg to 25 mg/kg (Category 3 Composition) which converts to a human equivalent dose of 6.8 mg/kg to 22.7 mg/kg. Accordingly, in the broad context of the present invention, the Category 3 Compositions herein are contemplated to provide an effective human equivalent dose for KCN exposure at dosage levels of 1.0 mg/kg to 25.0 mg/kg.

Figure 3:
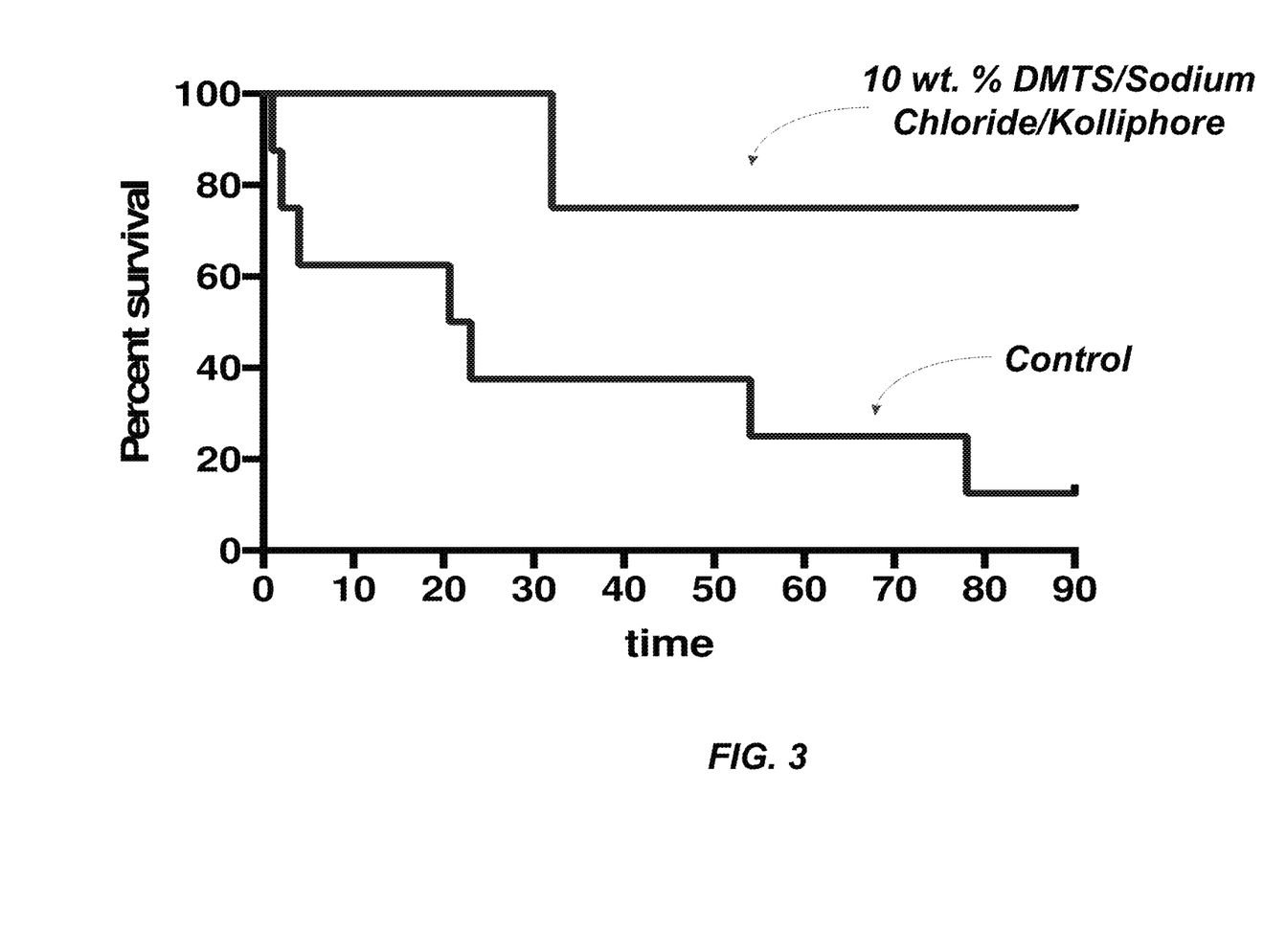
FIG. 3 illustrates the results of swine survival at a dose of 10 mg/kg of a composition containing 10.0 wt. % DMTS, 1.0 wt. % sodium chloride, 22.0 wt. % KOLLIPHORE® ELP versus a vehicle control (no antidote).

In addition, attention is next directed to FIG. 3 which identified the results of swine survival at a dose of 10 mg/kg of a composition containing 10.0 wt. % DMTS, 1.0 wt. % sodium chloride, 22.0 wt. % KOLLIPHORE® ELP versus a vehicle control (no antidote). As can be observed, swine survival 90 minutes after a 5 minute infusion of KCN showed a survival rate of around 75% as compared to the control survival rate of less than 20%.

While the invention herein has been disclosed with reference to various specific embodiments, it is apparent that other embodiments and variations may be devised by those skilled in the art.

What is claimed is:

1. A dimethyl trisulfide composition comprising a mixture of:
   dimethyl trisulfide at a level of 11 wt. % to 20 wt. %;
   sodium chloride at 1.0 wt. % to 10 wt. %;
   one or more non-ionic surfactants present at a level of 22 wt. % to 45 wt. %;
   the balance is water and wherein said composition includes a water miscible organic solvent at a level of up to and including 5000 ppm and said composition is a microemulsion containing dimethyl trisulfide droplets at a size of 1 nm to 100 nm and is present at a volume of 0.15 ml to 5.0 ml; and
   wherein said dimethyl trisulfide composition, when stored at a temperature of 20° C. to 25° C. in a sealed ampoule at said volume of 0.15 ml to 5.0 ml, provides that at least 90% or more by weight of the dimethyl trisulfide remains available for therapeutic use for a period up to and including 26 months.

2. The composition of claim 1 wherein said dimethyl trisulfide composition, when stored at a temperature of 20° C. to 25° C. in a sealed ampoule provides that at least 95% or more by weight of the dimethyl trisulfide remains available for therapeutic use.

3. The composition of claim 1 wherein the level of one or more non-ionic surfactants is present at a level of 25 wt. % to 45 wt. %.

4. The composition of claim 1 wherein the level of one or more non-ionic surfactants is present at a level of 30 wt. % to 45 wt. %.

5. The composition of claim 1 wherein the level of one or more non-ionic surfactants is present at a level of 35 wt. % to 45 wt. %.

6. The composition of claim 1 wherein the level of water is in the range of 25 wt. % to 67.9 wt. %.

7. A method of treating cyanide intoxication in a subject comprising administering to a subject who would benefit from such treatment an organic-solvent free composition comprising:
   dimethyl trisulfide at 11 wt. % to 20 wt. %;
   sodium chloride at 1.0 wt. % to 10 wt. %;
   one or more non-ionic surfactants present at a level of 22 wt. % to 45 wt. %;
   the balance is water wherein said composition includes a water miscible organic solvent at a level of up to and including 5000 ppm and said composition is a microemulsion containing dimethyl trisulfide droplets at a size of 1 nm to 100 nm and is present at a volume of 0.15 ml to 5.0 ml; and wherein said dimethyl trisulfide composition, when stored at a temperature of 20° C. to 25° C. in a sealed ampoule at said volume of 0.15 ml to 5.0 ml provides that at least 90% or more by weight of the dimethyl trisulfide remains available for therapeutic use for a period of up to and including twenty-six moths.

8. The method of claim 7 wherein said dimethyl trisulfide composition, when stored at a temperature of 20° C. to 25° C. in a sealed ampoule provides that at least 95% or more by weight of the dimethyl trisulfide remains available for therapeutic use for a period of up to and including twenty-six months.

9. The method of claim 7 wherein said subject is human and said composition is administered to said human subject at a dosage of 1.0 mg/kg to 25.0 mg/kg.

10. An autoinjector comprising an injection volume of 0.15 ml to 5.00 ml, said autoinjector configured to deliver a dose of a composition upon activation by an individual, the composition comprising,
    dimethyl trisulfide at 11 wt. % to 20 wt. %;
    sodium chloride at 1.0 wt. % to 10 wt. %;
    one or more non-ionic surfactants present at a level of 22 wt. % to 45 wt. %;
    the balance is water wherein said composition includes a water miscible organic solvent at a level of up to and including 5000 ppm and said composition is a microemulsion containing dimethyl trisulfide droplets at a size of 1 nm to 100 nm and is present at a volume of 0.15 ml to 5.0 ml; and wherein said dimethyl trisulfide composition, when stored at a temperature of 20° C. to 25° C. in a sealed ampoule at said volume of 0.15 ml to 5.0 ml provides that at least 90% or more by weight of the dimethyl trisulfide remains available for therapeutic use for a period of up to and including twenty-six moths.

11. The autoinjector of claim 10 wherein said dimethyl trisulfide composition, when stored at a temperature of 20° C. to 25° C. in said autoinjector provides that at least 95% or more by weight of the dimethyl trisulfide remains available for therapeutic use.

12. The autoinjector of claim 10, wherein said dimethyl trisulfide composition, when stored at a temperature of 40° C. in said autoinjector provides that at least 95% or more by weight of the dimethyl trisulfide remains available for therapeutic for a period of up to and including six months.

13. The composition of claim 1 wherein said composition is free of organic solvent.

* * * * *